US008927988B2

(12) United States Patent
Dang et al.

(10) Patent No.: US 8,927,988 B2
(45) Date of Patent: Jan. 6, 2015

(54) SELF-SEALED FLUIDIC CHANNELS FOR A NANOPORE ARRAY

(75) Inventors: Bing Dang, Chappaqua, NY (US); Hongbo Peng, Chappaqua, NY (US)

(73) Assignee: International Business Machines Corporation, Armonk, NY (US)

(*) Notice: Subject to any disclaimer, the term of this patent is extended or adjusted under 35 U.S.C. 154(b) by 124 days.

(21) Appl. No.: 13/606,904

(22) Filed: Sep. 7, 2012

(65) Prior Publication Data

US 2012/0326247 A1     Dec. 27, 2012

Related U.S. Application Data

(62) Division of application No. 13/092,424, filed on Apr. 22, 2011, now Pat. No. 8,518,829.

(51) Int. Cl.
*H01L 23/58* (2006.01)
*B82Y 15/00* (2011.01)
*G01N 33/487* (2006.01)

(52) U.S. Cl.
CPC .......... *B82Y 15/00* (2013.01); *G01N 33/48721* (2013.01); *Y10S 977/70* (2013.01); *Y10S 977/704* (2013.01); *Y10S 977/856* (2013.01); *Y10S 977/84* (2013.01); *Y10S 977/712* (2013.01)
USPC .......... 257/48; 257/9; 257/E21.001; 977/700; 977/704; 977/856; 977/840; 977/712

(58) Field of Classification Search
CPC .... C12Q 1/6869; G01B 33/48; G01N 33/482; G01N 33/48721; B82Y 40/00; B82Y 15/00
USPC ........ 257/9, 48, E21.001; 977/700, 704, 712, 977/840, 856, 857, 938
See application file for complete search history.

(56) References Cited

U.S. PATENT DOCUMENTS

| 5,753,014 A | 5/1998 | Van Rijn |
| 6,503,409 B1 | 1/2003 | Fleming |

(Continued)

FOREIGN PATENT DOCUMENTS

| CN | 1619834 A | 5/2005 |
| CN | 101203740 A | 6/2008 |

(Continued)

OTHER PUBLICATIONS

Chinese Office Action for corresponding Chinese Application No. 201110130886.8, dated Jun. 7, 2013, pp. 1-9.

(Continued)

*Primary Examiner* — Galina Yushina
(74) *Attorney, Agent, or Firm* — Cantor Colburn LLP; Vazken Alexanian

(57) ABSTRACT

A method of forming a nanopore array includes patterning a front layer of a substrate to form front trenches, the substrate including a buried layer disposed between the front layer and a back layer; depositing a membrane layer over the patterned front layer and in the front trenches; patterning the back layer and the buried layer to form back trenches, the back trenches being aligned with the front trenches; forming a plurality of nanopores through the membrane layer; depositing a sacrificial material in the front trenches and the back trenches; depositing front and back insulating layers over the sacrificial material; and heating the sacrificial material to a decomposition temperature of the sacrificial material to remove the sacrificial material and form pairs of front and back channels, wherein the front channel of each channel pair is connected to the back channel of its respective channel pair by an individual nanopore.

6 Claims, 15 Drawing Sheets

(56) References Cited

U.S. PATENT DOCUMENTS

| | | | |
|---|---|---|---|
| 6,541,353 | B1 | 4/2003 | Sandhu et al. |
| 6,579,752 | B2 | 6/2003 | De Boer |
| 6,709,929 | B2 | 3/2004 | Zhang et al. |
| 6,797,187 | B1 | 9/2004 | Galambos et al. |
| 6,827,866 | B1 | 12/2004 | Novotny |
| 6,846,702 | B1 | 1/2005 | Barth |
| 6,887,391 | B1 | 5/2005 | Daneman et al. |
| 7,001,792 | B2 | 2/2006 | Sauer et al. |
| 7,052,821 | B2 | 5/2006 | Kohl et al. |
| 7,138,672 | B2 | 11/2006 | Barth |
| 7,250,115 | B2 | 7/2007 | Barth |
| 7,468,271 | B2 | 12/2008 | Golovchenko et al. |
| 7,553,730 | B2 | 6/2009 | Barth et al. |
| 7,625,706 | B2 | 12/2009 | Akeson et al. |
| 7,638,345 | B2 | 12/2009 | Lee et al. |
| 7,678,562 | B2 | 3/2010 | Ling |
| 7,765,679 | B2 | 8/2010 | Yao et al. |
| 2003/0029839 | A1 | 2/2003 | Chou |
| 2003/0104428 | A1 | 6/2003 | Branton et al. |
| 2005/0103713 | A1 | 5/2005 | Ramsey et al. |
| 2005/0170670 | A1 | 8/2005 | King et al. |
| 2006/0154399 | A1* | 7/2006 | Sauer et al. ............... 438/48 |
| 2007/0042366 | A1 | 2/2007 | Ling |
| 2007/0178507 | A1 | 8/2007 | Wu et al. |
| 2007/0190542 | A1 | 8/2007 | Ling et al. |
| 2007/0199341 | A1* | 8/2007 | Hart ............................ 62/260 |
| 2008/0121534 | A1* | 5/2008 | White et al. ............. 205/787.5 |
| 2008/0171316 | A1* | 7/2008 | Golovchenko et al. ........ 435/6 |
| 2008/0251877 | A1 | 10/2008 | Jain et al. |
| 2008/0254995 | A1* | 10/2008 | Kim et al. ...................... 506/4 |
| 2009/0136958 | A1 | 5/2009 | Gershow et al. |
| 2010/0026779 | A1 | 2/2010 | Yonehara et al. |
| 2010/0127390 | A1 | 5/2010 | Barth |
| 2010/0327255 | A1 | 12/2010 | Peng et al. |
| 2010/0331194 | A1* | 12/2010 | Turner et al. .................... 506/2 |
| 2011/0033952 | A1 | 2/2011 | Khater et al. |
| 2011/0048947 | A1 | 3/2011 | Petronis et al. |
| 2011/0279125 | A1 | 11/2011 | Bedell et al. |
| 2011/0308949 | A1 | 12/2011 | Afzali-Azdakani et al. |

FOREIGN PATENT DOCUMENTS

| | | |
|---|---|---|
| CN | 101668866 A | 3/2010 |
| WO | 2010020912 A1 | 2/2010 |
| WO | 2010117470 A2 | 10/2010 |

OTHER PUBLICATIONS

Chen, et al., "Mechanisms for Formation of a One-Dimensional Horizontal Anodic Aluminum Oxide Nanopore Array on a Si Substrate", J. Electrochem. Soc., vol. 152, No. 12, 2005, pp. D227-D231.

Jayachandran, et al., "Air-Channel Fabrication for Microelectromechanical Systems via Sacrificial Photosensitive Polycarbonates", Journal of Microelectromechanical Systems, vol. 12, No. 2, 2003, pp. 147-159.

Kasianowicz, et al., "Characterization of Individual Polynucleotide Molecules Using a Membrane Channel", Proc. Natl. Acad. Aci. USA, vol. 93, 1996, pp. 13770-13773.

Kim, et al., "Rapid Fabrication of Uniformly Sized Nanopores and Nanopore Arrays for Parellel DNA Analysis", Adv. Mater., vol. 18, 2006, pp. 3149-3153.

Li, et al., "Sacrificial Polymers for Nanofluidic Channels in Biological Applications", Nanotechnology, vol. 14, No. 6, 2003, pp. 578-583.

Gracheva M E, et al., "Simulation of the Electric Response of DNA Translocation Through a Semiconductor Nanopore-capacitor," Nanotechnology, 17, pp. 622-633 (2006).

Branton, et al., "The Potential and Challenges of Nanopore Sequencing," Nature biotechnology 26(10), pp. 1146-1153 (2008).

Bing Dang, "Integrated Thermal-Fluidic I/O Interconnects for an On-Chip Microchannel Heat Sink," IEEE EDL, 27(2), pp. 117-119 (2006).

Heng et al., "Sizing DNA Using a Nanometer-Diameter Pore," Biophysical Journal, vol. 87, Oct. 2004, pp. 2905-2911.

Lagerqvist, et al., "Fast DNA Sequencing via Transverse Electronic Transport," Nano Letters, 2006, vol. 6, No. 4, pp. 779-782.

Meller A, Nivon, et al.,"Rapid Nanopore Discrimination Between Single Polynucleotide Molecules," Proc. Natl Acad. Sci. USA, PNAS, vol. 97, No. 3, Feb. 2000, pp. 1079-1084.

Soni G and Meller, "Progress Towards Ultrafast DNA Sequencing Using Solid-State Nanopores," Clinical Chemistry, 53:11, pp. 1996-2001, 2007.

R. Akeson, et al.,"Microsecond Timescale Discrimination Among Polycytidylic Acid, Polyadenylic Acid, and Polyuridylic Acid as Homopolymers or as Segments within Single RNA Molecules," Biophysical Journal, vol. 77, Dec. 1999, pp. 3227-3233.

P. Bergveld, "Thirty Years of ISFETOLOGY: What Happened in the past 30 years and what may happen in the next 30 years," MESA, Sensors and Actuatorrs B 88, pp. 1-20, 2003.

Stefano Vassanelli, et al."Transistor Probes Local Potassium Conductances in the Adhesion Region of Cultured Rat Hippocampal Neurons," The Journal of Neuroscience, Aug. 1999, 19(16); pp. 1-7.

Johnny Ho, "Controlled Nanoscale Doping of Semiconductors via Molecular Monolayers," Nature Materials, vol. 7, pp. 1-16, Jan. 2008.

Jiali Li, et al., "Ion-beam Sculpting at Nanometre Length Scales," Letter; Nature, vol. 412, pp. 1-4, Jul. 2001.

Stern, et al., "Label-free immunodetection with CMOS-compatible semiconducting nanowires," nature Letters, Feb. 2007, pp. 519-522, vol. 445, Nature Publishing Group.

International Search Report; International Application No. PCT/US 12/28231; International Filing Date: Mar. 8, 2012; Date of Mailing: Jun. 15, 2012; pp. 1-5.

International Search Report—Written Opinion; International Application No. PCT/US 12/28231; International Filing Date: Mar. 8, 2012; Date of Mailing: Jun. 15, 2012; pp. 1-8.

H. Rucker, "Dopant Diffusion in C-doped Si and SiGe: Physical Model and Experimental Verification," IEEE, IEDM99-345, pp. 1-4, 1999.

A.J. Storm, et al., "Fabrication of Solid-State Nanopores with Single-Nanometre Precision," Nature Materials, Letters, vol. 2, pp. 1-5, Aug. 2003.

Uram et al., "Noise and Bandwidth of Current Recordings from Submicrometer Pores and Nanopores," ACS Nano, 2008, pp. 857-872, vol. 2, No. 5, American Chemical Society.

Headrick, "Si(100)-(2X1)boron reconstruction: Self-Limiting Monolayer Doping," Appl. Phys. Lett. 57, (26), pp. 1-4, Dec. 1990.

Sufi Zafar, et al., "Optimization of pH Sensing Using Silicon Nanowire Field Effect Transistors with HfO2 as the sensing Surface," Nanotechnology, 22, IOP Publishing, pp. 1-7, 2011.

Gunther Zeck, "Noninvasive Neuroelectronic Interfacing with Synaptically connected Snail Neurons Immobilized on a Semiconductor Chip," Neurobiolgy, PNAS, vol. 98, No. 18, pp. 1-6, Aug. 2001.

Patolsky et al., "Electrical detection of single viruses," PNAS, Sep. 28, 2004, pp. 14017-14022, vol. 101, No. 39, PNAS.org.

Polonsky, et al., "Nanopore in Metal-Dielectric Sandwich for DNA Position Control", Appl. Phys. Lett., vol. 91, 2007, 153103, pp. 153103-1-153103-3.

* cited by examiner

SELF-SEALED FLUIDIC CHANNELS FOR A NANOPORE ARRAY

CROSS-REFERENCE TO RELATED APPLICATION

This application is a divisional of U.S. patent application Ser. No. 13/092,424, filed Apr. 22, 2011, the disclosure of which is incorporated by reference herein in its entirety.

BACKGROUND

This disclosure relates generally to the field of sensors for sequencing deoxyribonucleic acid (DNA) and proteins.

DESCRIPTION OF RELATED ART

Mapping the sequence of bases of a DNA strand is of great importance in life sciences. Current DNA sequencing technologies based on sequencing by synthesis cost more than $300,000 per human genome, and there is great demand to lower the cost to less than $1000 per human genome for purposes such as personalized medicine and preventive Medicare. Since a single base is about 0.7 nanometers (nm) long when the DNA strand is stretched, it is important that a sensor for sequencing have a spatial resolution of about 1 nm or less. Fabricating a sensor with a spatial resolution in this range, however, is challenging. Another area of great importance in life sciences is detection of proteins and viruses. For protein and viruses detection, a biomolecule sensor that comprises a field effect transistor (FET) may be used. However, a disadvantage of many FET-based sensors is that a sensing surface of the sensor must be covered with a biological coating that specifically binds the biomolecules to be detected. Applying the appropriate coating may be labor intensive and expensive. Further, the FET sensor may only be used to detect the particular biomolecules that bind with the coating, limiting the usefulness of the sensor.

A FET sensor may comprise highly doped source and drain regions formed by ion implantation, and followed by high temperature annealing (e.g., about 1000° C.). Though this method is standard for forming source and drain regions in longer channel (greater than 10 nm) FET devices, ion implantation and anneal may pose a problem for fabrication of relatively short FET channels (less than about 5 nm) required for high sensitivity FET devices, as ion implantation and high temperature activation annealing produce dopant density profiles in the source/drain regions that may extend several nanometers into the channel region of the FET. Consequently, the sensitivity of a FET sensor formed in this manner may be degraded, making the FET sensor inappropriate for use for sequencing DNA.

A nanopore sensor has been proposed as a potential approach for DNA sequencing at cost less than $1000 per human genome, and may be used as an alternative to a FET sensor for biomolecule sensing. Because DNA molecules have a relatively high negative charge, a DNA molecule may be electrically driven from a first fluidic reservoir to a second fluidic reservoir through a nanopore that has a diameter on the order of a few nanometers. FIG. 1 shows a nanopore sensor system 100 including a single nanopore 103 according to the prior art. The nanopore 103 is formed through a membrane 101. The membrane 101 partitions a fluidic reservoir 104 into two parts: top reservoir 105 and bottom reservoir 106. The fluidic reservoir 104 and the nanopore 103 are then filled with a fluid 107, which may be an ionic buffer, which contains biomolecules such as DNA molecule 108. The DNA molecule 108 is translocated through nanopore 103 by an electrical voltage bias 109 that is applied across the nanopore 103 via two electrochemical electrodes 110 and 111, which are dipped in the top fluid reservoir 105 and the bottom fluid reservoir 106, respectively. As the DNA molecule 108 moves through the nanopore 103, the DNA molecule 108 is sequenced via ionic current through the nanopore or other optical/electrical sensors integrated near the nanopore 103. Besides DNA sequencing, such nanopore sensors may perform relatively rapid analysis of biomolecules, such as DNA, RNA, and proteins, in addition to providing information regarding biomolecule interactions. Nanopore DNA sequencing is a real-time single molecule method, without the need of DNA amplification or chemically modifying the DNA, and offers a relatively lowest cost method for DNA sequencing.

BRIEF SUMMARY

In one aspect, a method of forming a nanopore array includes patterning a front layer of a substrate to form front trenches, the substrate including a buried layer disposed between the front layer and a back layer; depositing a membrane layer over the patterned front layer and in the front trenches; patterning the back layer and the buried layer to form back trenches, the back trenches being aligned with the front trenches; forming a plurality of nanopores of the nanopore array through the membrane layer; depositing a sacrificial material in the front trenches and the back trenches; depositing front and back insulating layers over the sacrificial material; and heating the sacrificial material to a decomposition temperature of the sacrificial material to remove the sacrificial material and form pairs of front and back channels, wherein the front channel of each channel pair is connected to the back channel of its respective channel pair by an individual nanopore.

In another aspect, a nanopore array includes a plurality of front and back channel pairs located in a substrate, wherein the front channel of each channel pair is connected to the back channel of its respective channel pair by a single nanopore of a plurality of nanopores, wherein the nanopores are formed through a membrane layer that is located between the front channels and the back channels; wherein the plurality of front channels of the plurality of front and back channel pairs are located in a patterned front layer of the substrate and bounded on top by a front insulating layer; wherein the membrane layer is located over the patterned front layer and in a bottom portion of the plurality of front channels; and wherein the plurality of back channels of the plurality of front and back channel pairs are located in a patterned buried layer and a patterned back layer of the substrate and bounded at the bottom by a back insulating layer.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of self-sealed fluidic channels for a nanopore array and methods of making self-sealed channels for a nanopore array are provided, with exemplary embodiments being discussed below in detail. Each human genome has about 3 billion base pairs, requiring breaking the genome into many parts and sequencing the parts in parallel to reduce the overall sequencing time and increase sequencing throughput. An array of individually addressable nanopores in conjunction with self-sealed channels for DNA sequencing may significantly reduce the cost and time required for sequencing a human genome by allowing sequencing to be performed in parallel by the various nanopores of the nanopore array. The self-sealed channels act as the fluidic reservoirs for the nanopores in the nanopore array, and are formed by integrated circuit (IC) manufacturing methods using a sacrificial material without the need for wafer bonding. Because the self-sealed channels are relatively small, the physical size of the conductive fluidics containing the DNA are also relatively small, thus reducing parasitic capacitance between the electrodes for high frequency applications.

Figure 1:
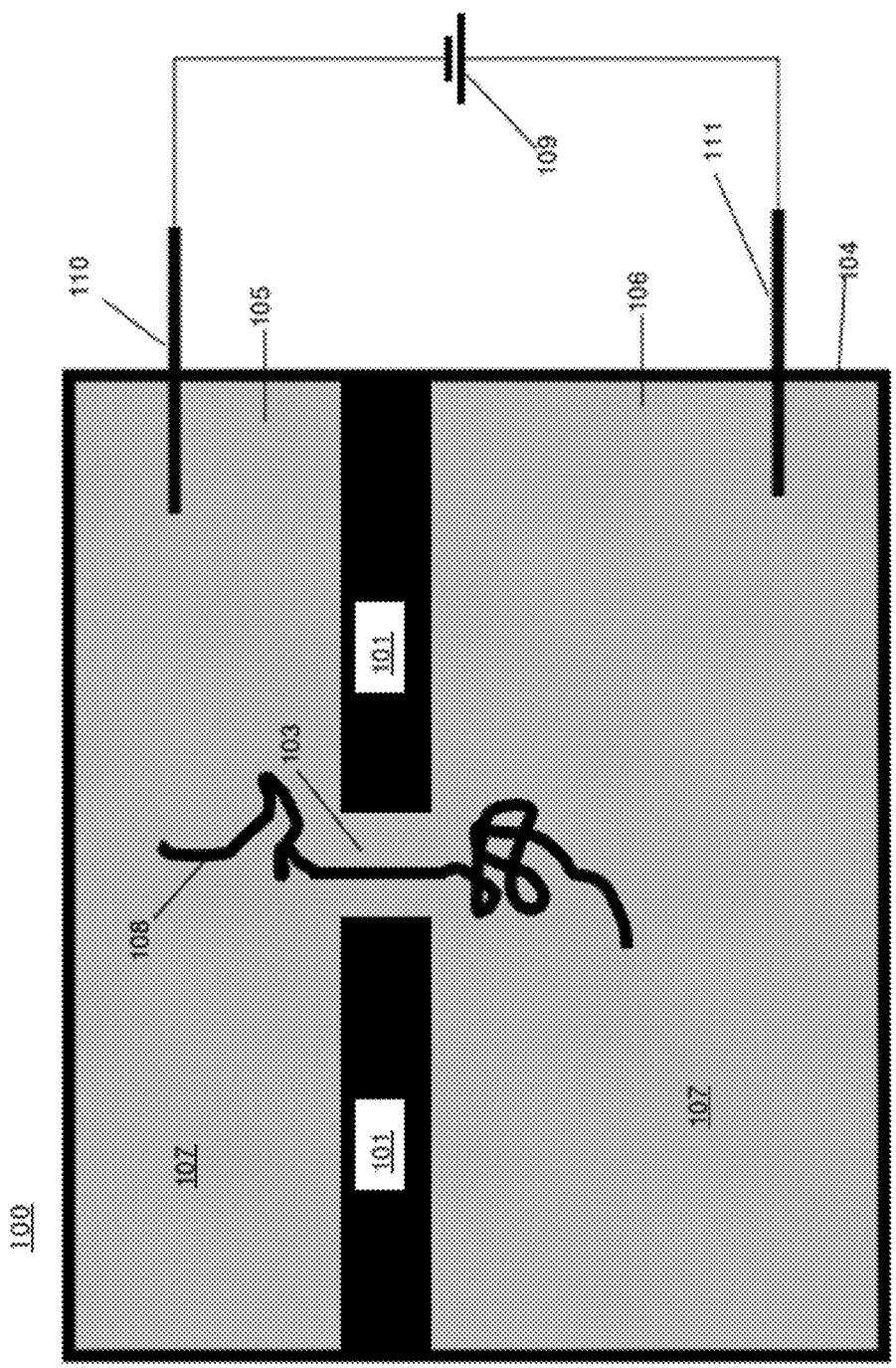
FIG. 1 is a schematic diagram illustrating a cross section of an embodiment of a nanopore sensor system for DNA sequencing according to the prior art.
Figure 2:
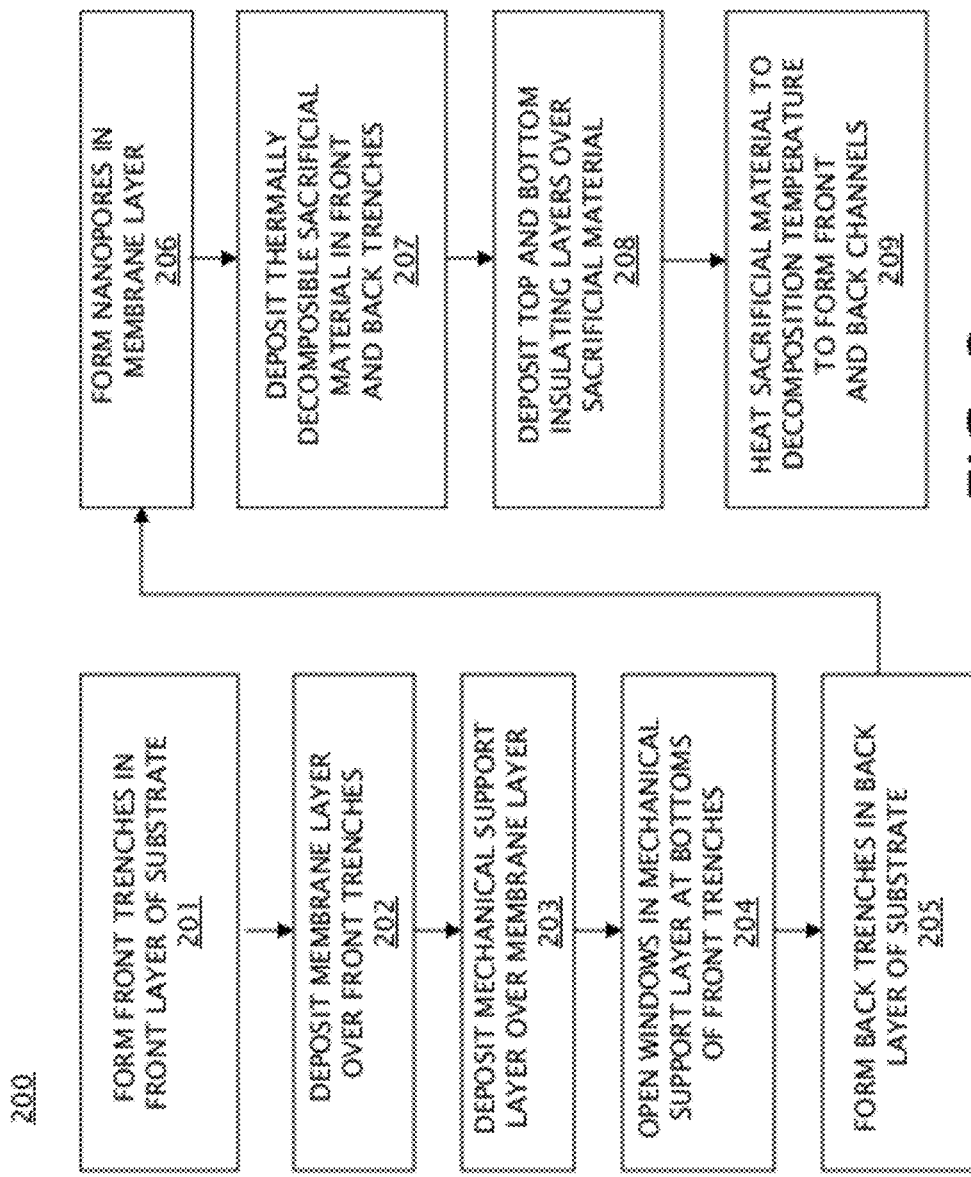
FIG. 2 is a flowchart illustrating an embodiment of a method of forming self-sealed fluidic channels for a nanopore array.
Figure 3:
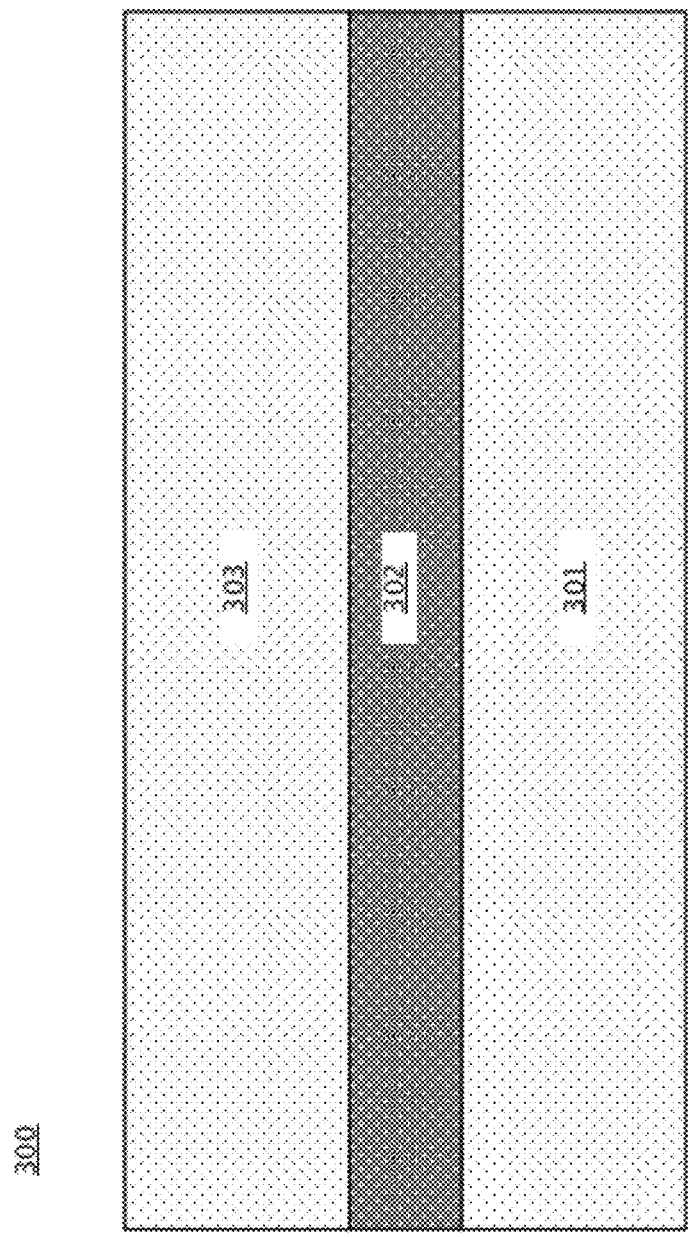
FIG. 3 is a schematic diagram illustrating a cross section of an embodiment of a substrate.
Figure 4:
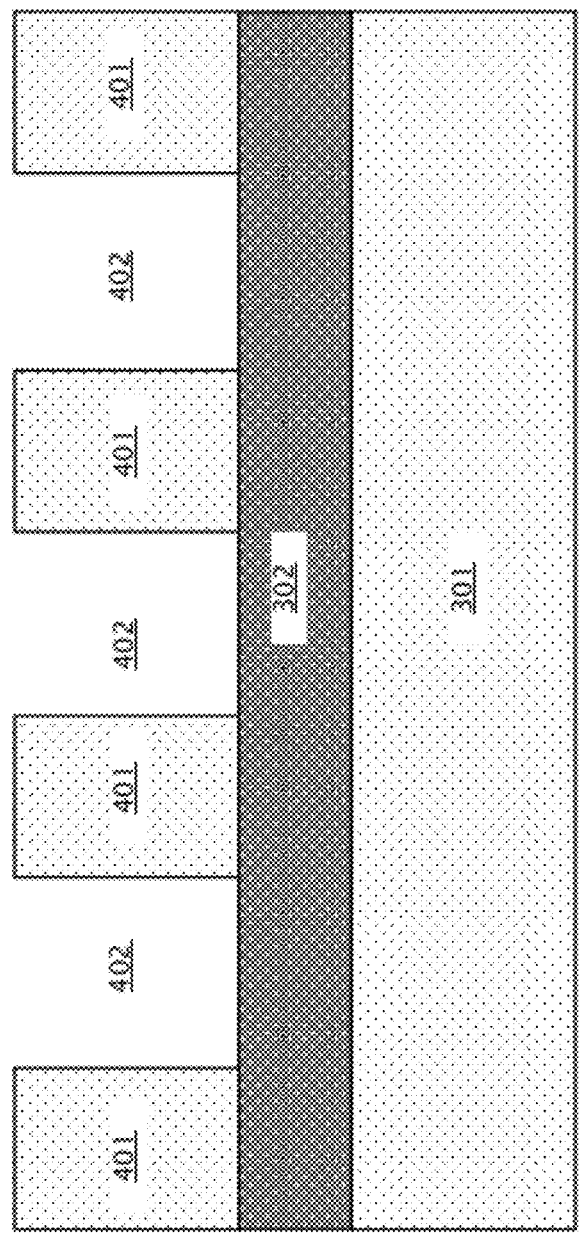
FIG. 4 is a schematic diagram illustrating a cross section of the substrate of FIG. 3 after patterning the front layer of the substrate to form front trenches.
Figure 5:
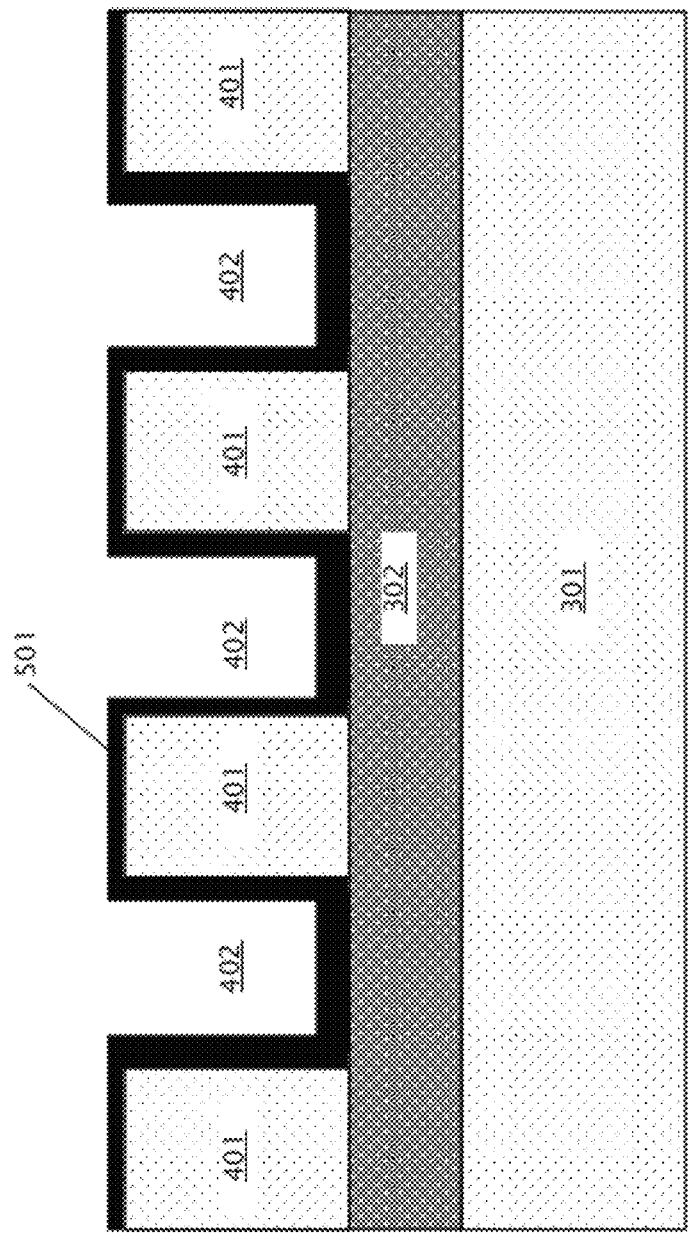
FIG. 5 is a schematic diagram illustrating a cross section of the device of FIG. 4 after depositing of a membrane layer over the patterned front layer and the front trenches.
Figure 6:
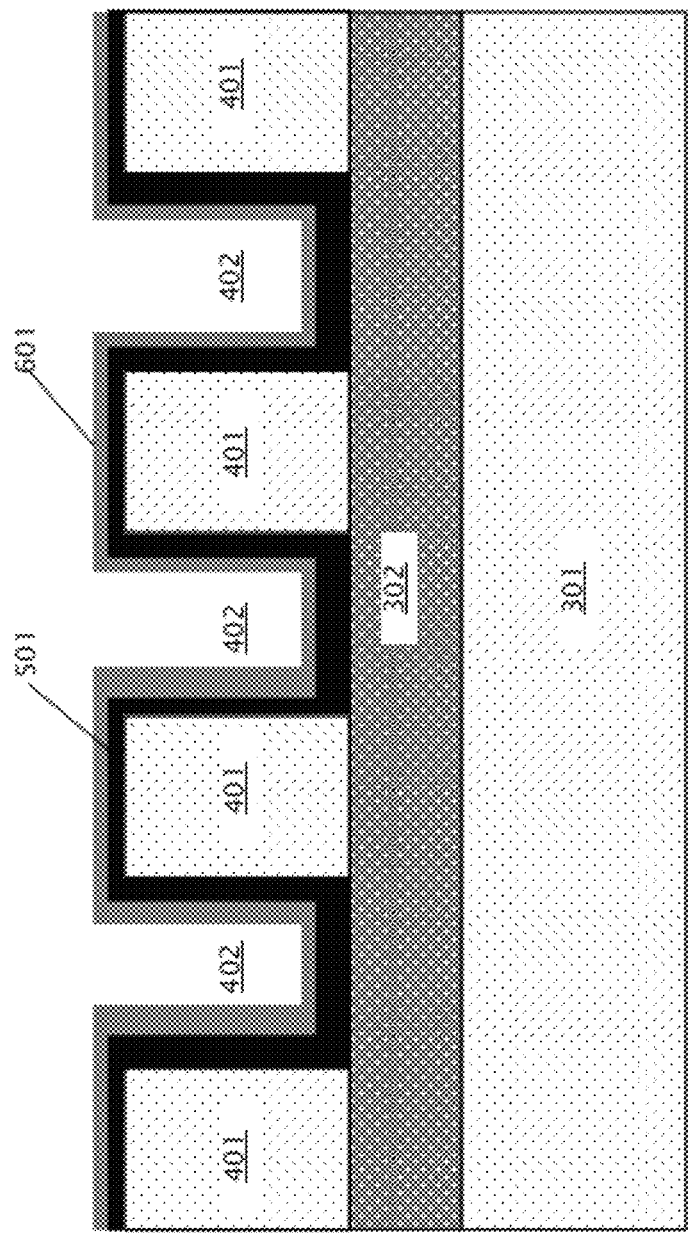
FIG. 6 is a schematic diagram illustrating a cross section of the device of FIG. 5 after formation of a mechanical support layer over the membrane layer.
Figure 7:
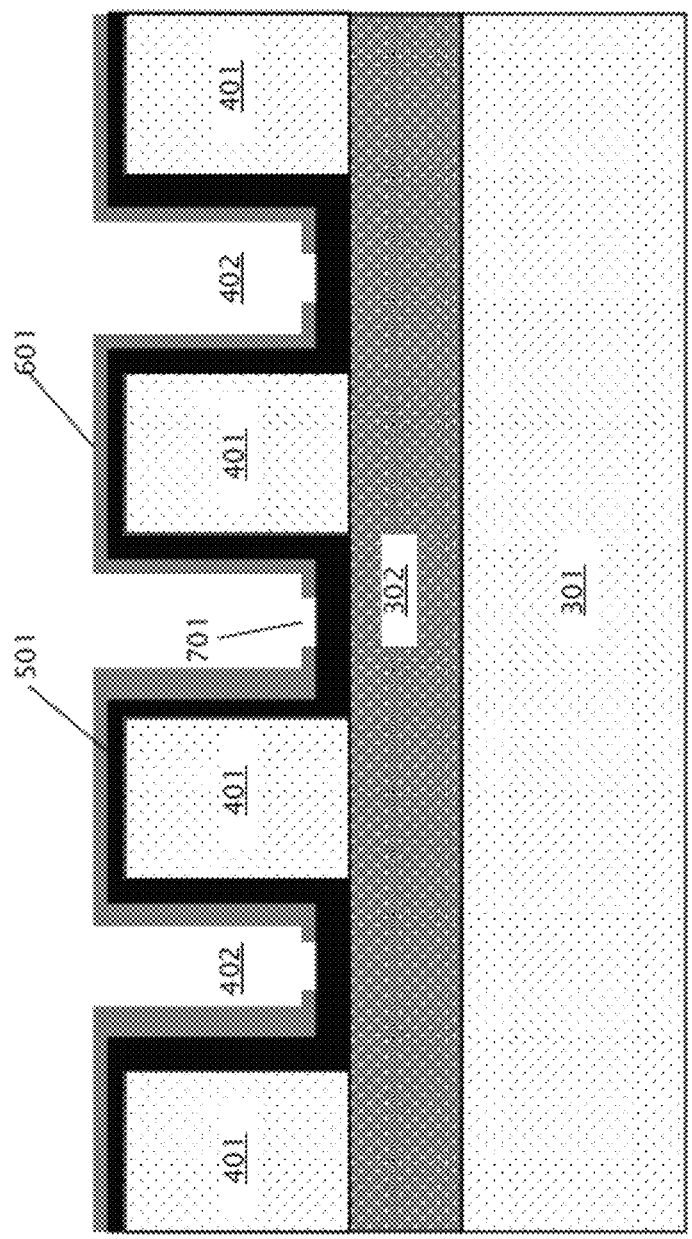
FIG. 7 is a schematic diagram illustrating a cross section of the device of FIG. 6 after opening windows in the mechanical support layer.
Figure 8:
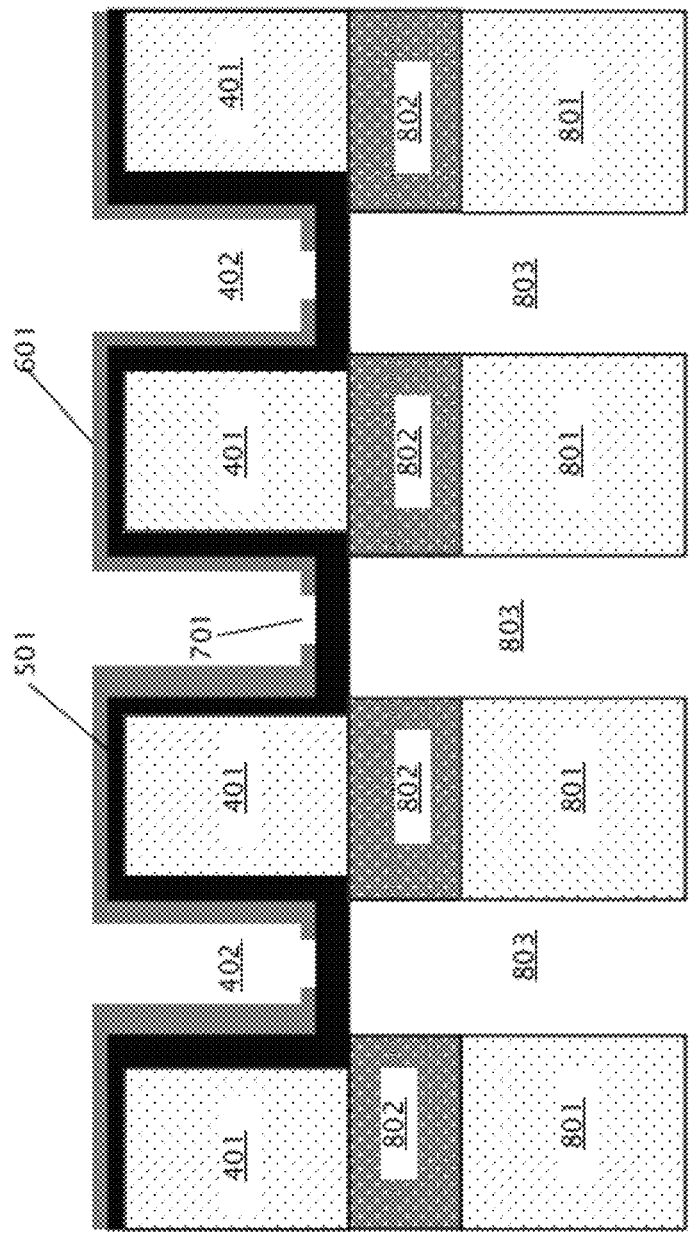
FIG. 8 is a schematic diagram illustrating a cross section of the device of FIG. 7 after patterning the back layer and the buried layer of the substrate to form back trenches.

Turning to FIG. 2, a flowchart illustrating an embodiment of a method 200 of forming a nanopore array with self-sealed fluidic channels is shown. FIG. 2 is discussed with reference to FIGS. 3-12. Initially, a substrate, or wafer, as is shown in FIG. 3, is provided. Substrate 300 of FIG. 3 includes a back layer 301 and front layer 303, with a buried layer 302 located between the front layer 303 and the back layer 301. Front layer 301, buried layer 302, and back layer 303 may be any appropriate solid state materials so long as front layer 301 and back layer 303 are different materials from buried layer 302. Substrate 300 may include a silicon-on-insulator (SOI) substrate in some embodiments, in which back layer 301 and front layer 303 are silicon, which may be doped or undoped silicon in various embodiments, and buried layer 302 is silicon oxide. In other embodiments, back layer 301 and front layer 303 may include any appropriate semiconductor materials, and may be different materials, and buried layer 302 may include any appropriate insulating material. In block 201 of FIG. 2, the front layer 303 is patterned to form trenches, resulting in patterned front layer 401 with front trenches 402 located between patterned front layer 401, as shown in FIG. 4. The patterned front layer 401 and front trenches 402 may be formed by etching into the front layer 303 and stopping on the buried layer 302; this may be accomplished, for example, by deep ultraviolet (DUV) photolithography and reactive ion etching (RIE).

As indicated in block 202 of FIG. 2, a membrane layer is deposited over the patterned front layer 401 of FIG. 4. As more specifically illustrated in FIG. 5, the membrane layer 501 is deposited over patterned front layer 401 and in the front trenches 402 on the buried layer 302. Membrane layer 501 may be an insulating material including, but not limited to, silicon nitride in some embodiments, or may be graphene in other embodiments. The thickness of membrane layer 501 is selected such that nanopores may be formed in the membrane layer 501 (discussed in further detail below with respect to block 206), and may be about 200 nanometers thick or less. More specifically, a silicon nitride membrane layer 501 may be about 20 nm thick in some exemplary embodiments, or membrane layer 501 comprising a single layer of graphene may be about 0.335 nm thick. It should be noted that the membrane layer 501 is selected to be a different material with respect to the buried layer 302.

After formation of the membrane layer 501, a mechanical support layer is formed over the membrane layer 501, as generally indicated in block 203 of FIG. 2. As specifically shown in FIG. 6, mechanical support layer 601 is deposited over membrane layer 501. Mechanical support layer 601 is relatively thick as compared to membrane layer 501, and may include one or multiple layers in various embodiments. For example, mechanical support layer 601 may include a bottom layer of silicon oxide (that may be about 200 nm thick, for example) located adjacent to membrane layer 501, and a top layer of silicon nitride (that may also be about 200 nm thick, for example) located over the layer of silicon oxide. The thickness of the mechanical supporting layer may vary from nanometers to microns depending on the application and the employed material(s). For example, formation of a relatively thick mechanical support layer 601 may reduce ionic current noise in a nanopore sensor system during operation. While the mechanical support layer 601 may include any appropriate insulating material in various embodiments, the portion of mechanical support layer 601 that is adjacent to membrane layer 501 is a material that is different to the material that comprises membrane layer 501 to allow selective etching of the mechanical support layer 601 while stopping on the membrane layer 501.

Next, as indicated in block 204 of FIG. 2, windows are opened in the mechanical support layer 601 corresponding to location at the bottoms of front trenches 402. As specifically shown in FIG. 7, the windows, such as window 701, are etched into the mechanical support layer 601 to expose the front side of membrane layer 501. Windows 701 are formed by, for example, wet and/or dry etching in various embodiments. In embodiments in which mechanical support layer 601 includes a bottom layer of silicon oxide located adjacent to membrane layer 501, and a top layer of silicon nitride located over the layer of silicon oxide, the dry etch (such as carbon tetraflouride based reactive ion etching) may first be used to open the top layer of silicon nitride, and then a wet etch (such as hydrofluoric etchant) may be used to open up the bottom layer of silicon oxide; the wet etch stops when membrane layer 501 is reached.

Next, as indicated in block 205 of FIG. 2, the back layer 301 and buried layer 302 are patterned to form back trenches that are aligned with front trenches 402. As specifically shown in FIG. 8, the back trenches 803 are located between patterned back layer 801 and patterned buried layer 802, and expose the back side of membrane layer 501. Back trenches 803 are aligned with front trenches 402. Back trenches 803 may be formed by etching into back layer 301 and stopping on the buried layer 302, which may be accomplished by DUV photolithography and RIE, thereby defining patterned back material 801. This exposes a portion of the back surface of buried layer 302, which can be dry or wet etched to remove the exposed portion of the buried layer 302 on the back side of the substrate, in turn forming patterned buried layer 802. Back trenches 803 expose the back side of membrane layer 501.

After formation of the back trenches 803, both the front and back sides of membrane layer 501 are exposed, allowing formation of nanopores in membrane layer 501, as indicated in block 206 of FIG. 2. As specifically shown in FIG. 9, the nanopores 901 that are formed in membrane layer 501 connect the front trenches 402 with the back trenches 803. The nanopores may be formed in membrane layer 501 using a focused electron beam from a transmission electron microscope (TEM) in some embodiments. The beam from a TEM is relatively small, for example on the order of a few nanometers in diameter in some embodiments, allowing formation of commensurately small nanopores 901 in membrane layer 501. In other embodiments, the nanopores 901 may be formed in membrane layer 501 by focused ion beam sculpting or RIE with a hard mask. Nanopores 901 typically have sizes ranging from sub-nanometer to tens of nanometers.

Figure 9:
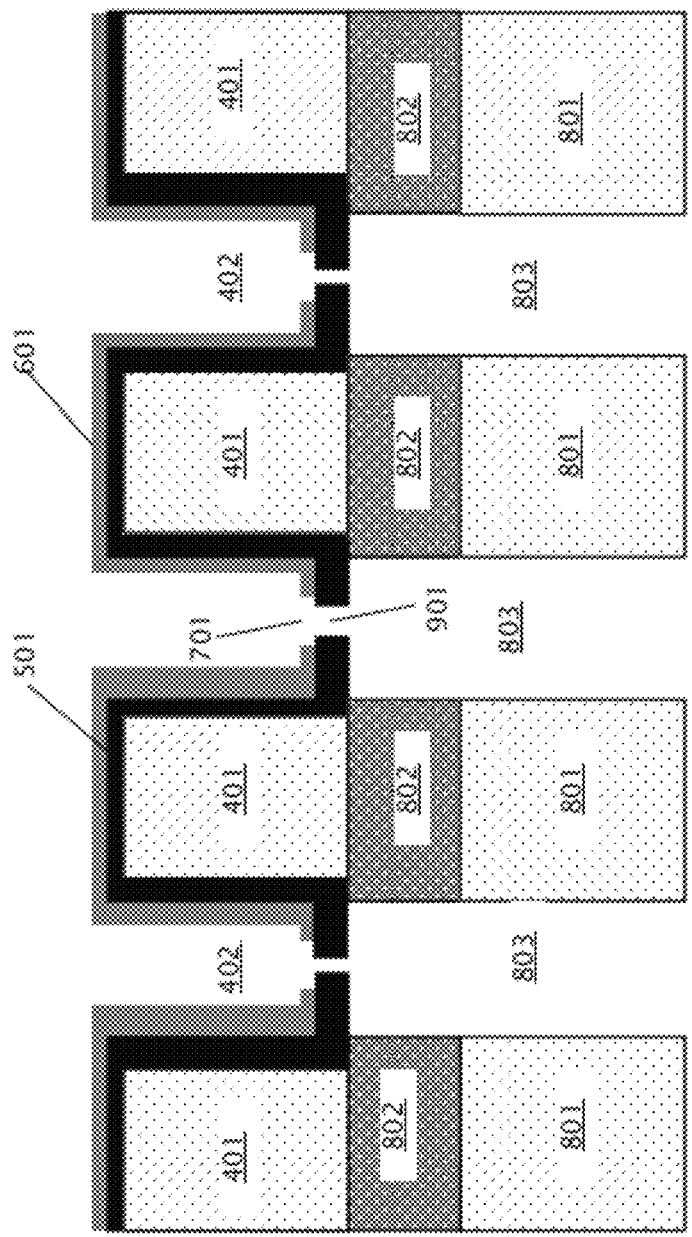
FIG. 9 is a schematic diagram illustrating a cross section of the device of FIG. 8 after forming nanopores in the membrane layer.
Figure 10:
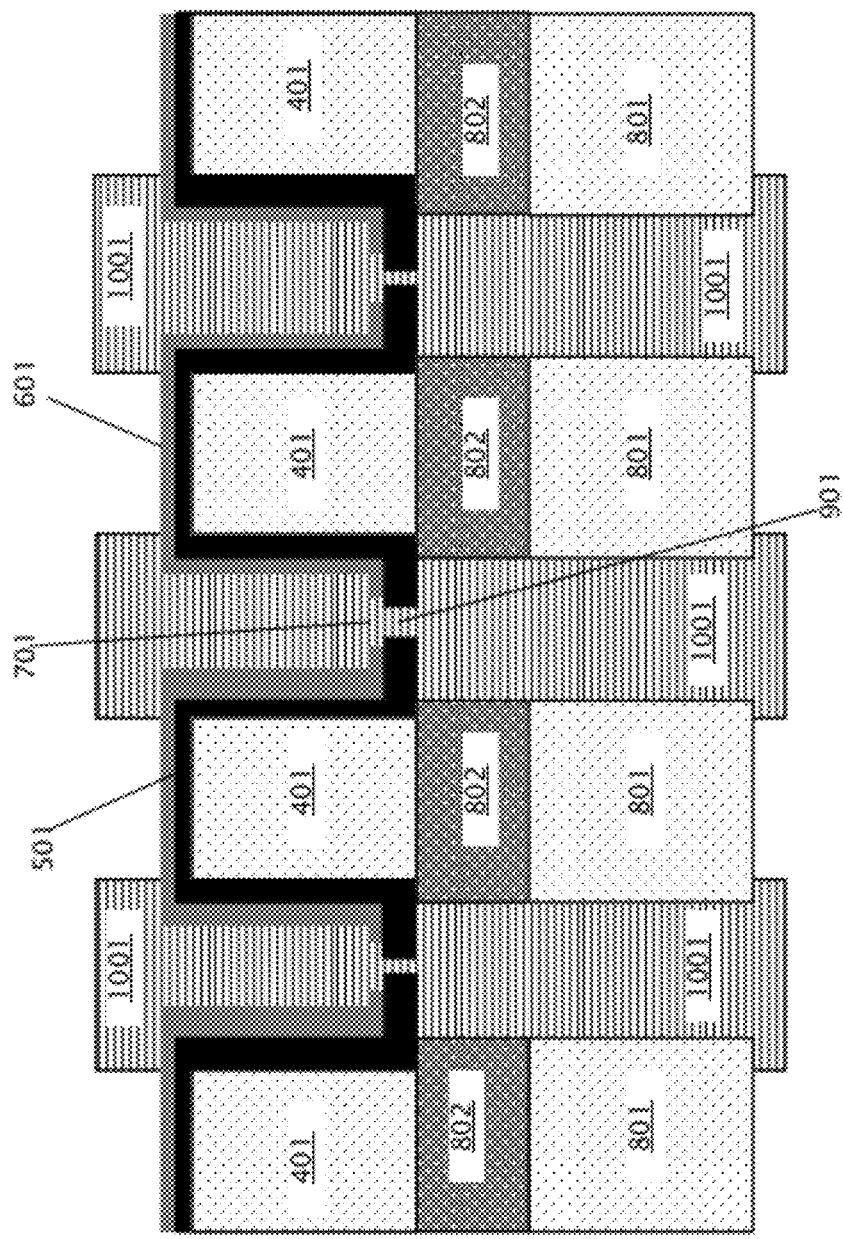
FIG. 10 is a schematic diagram illustrating a cross section of the device of FIG. 9 after deposition of a thermally decomposable sacrificial material in the front and back trenches.
Figure 11:
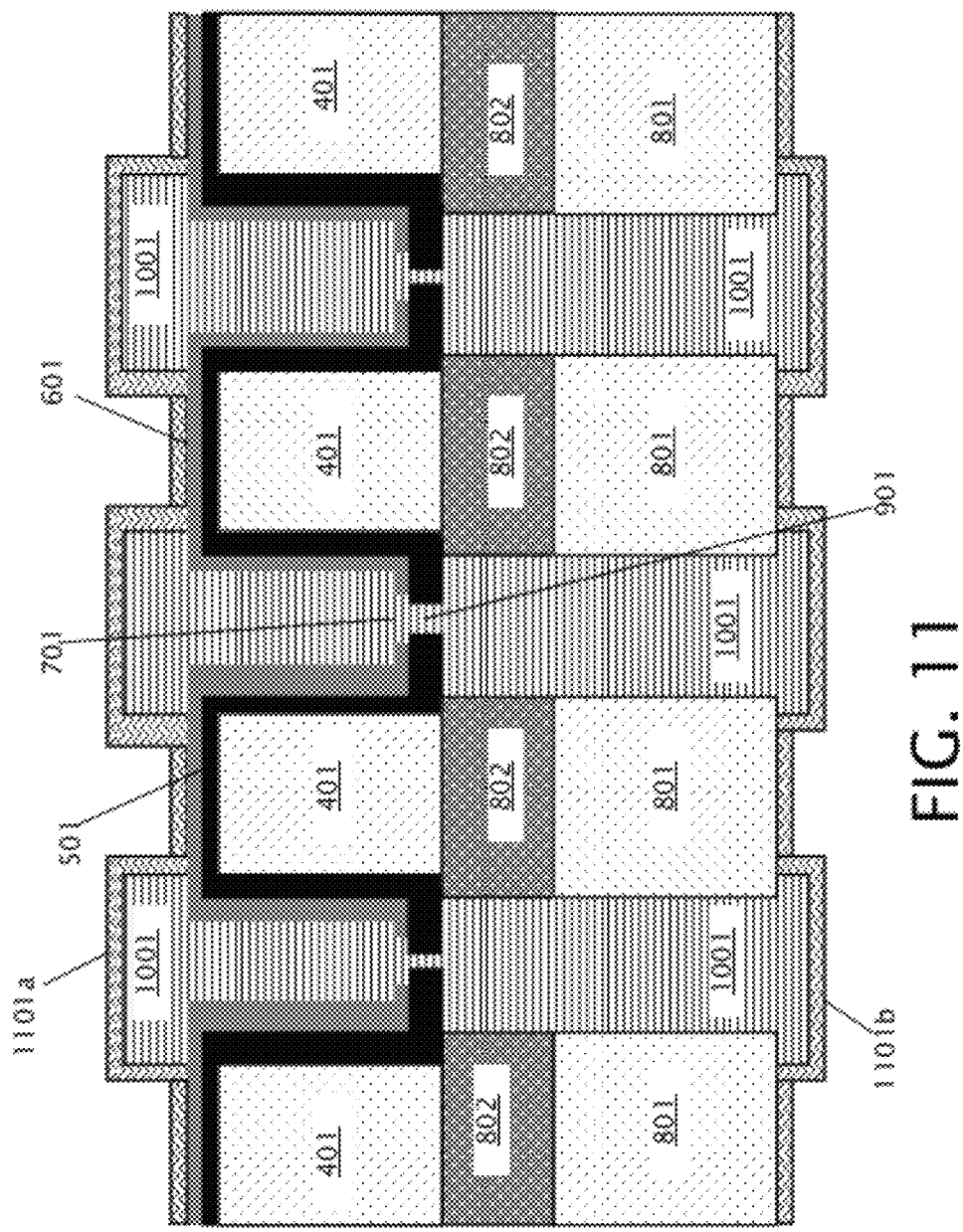
FIG. 11 is a schematic diagram illustrating a cross section of the device of FIG. 10 after deposition of an insulating material over the front and back sacrificial material.

Then, as indicated in block 207 of FIG. 2, a sacrificial material is deposited over the front and back of the structure of FIG. 9, including the front trenches 402, back trenches 803, and nanopores 901. FIG. 10 shows the device of FIG. 9 after deposition of the sacrificial material 1001. The sacrificial material 1001 may be patterned after deposition to expose the top surface of the mechanical support layer 601. Sacrificial material 1001 includes a thermally decomposable material, which may include a polycarbonate in some embodiments (discussed in further detail below with respect to FIGS. 15a-b). Sacrificial material 1001 may be deposited by spin coating, for example.

Next, as indicated in block 208 of FIG. 2, front and back insulating layers are deposited over the front and back surfaces of the structure of FIG. 10. As specifically shown in FIG. 11, the front insulating layer 1101a covers the top surface of the sacrificial material 1001 and the mechanical support layer 601 on the front side of the device, and the back insulating layer 1101b covers the bottom portions of the sacrificial material 1001 and the patterned back layer 801 on the back side of the device. Front and back insulating layers 1101a-b may be silicon nitride in some embodiments.

Figure 12:
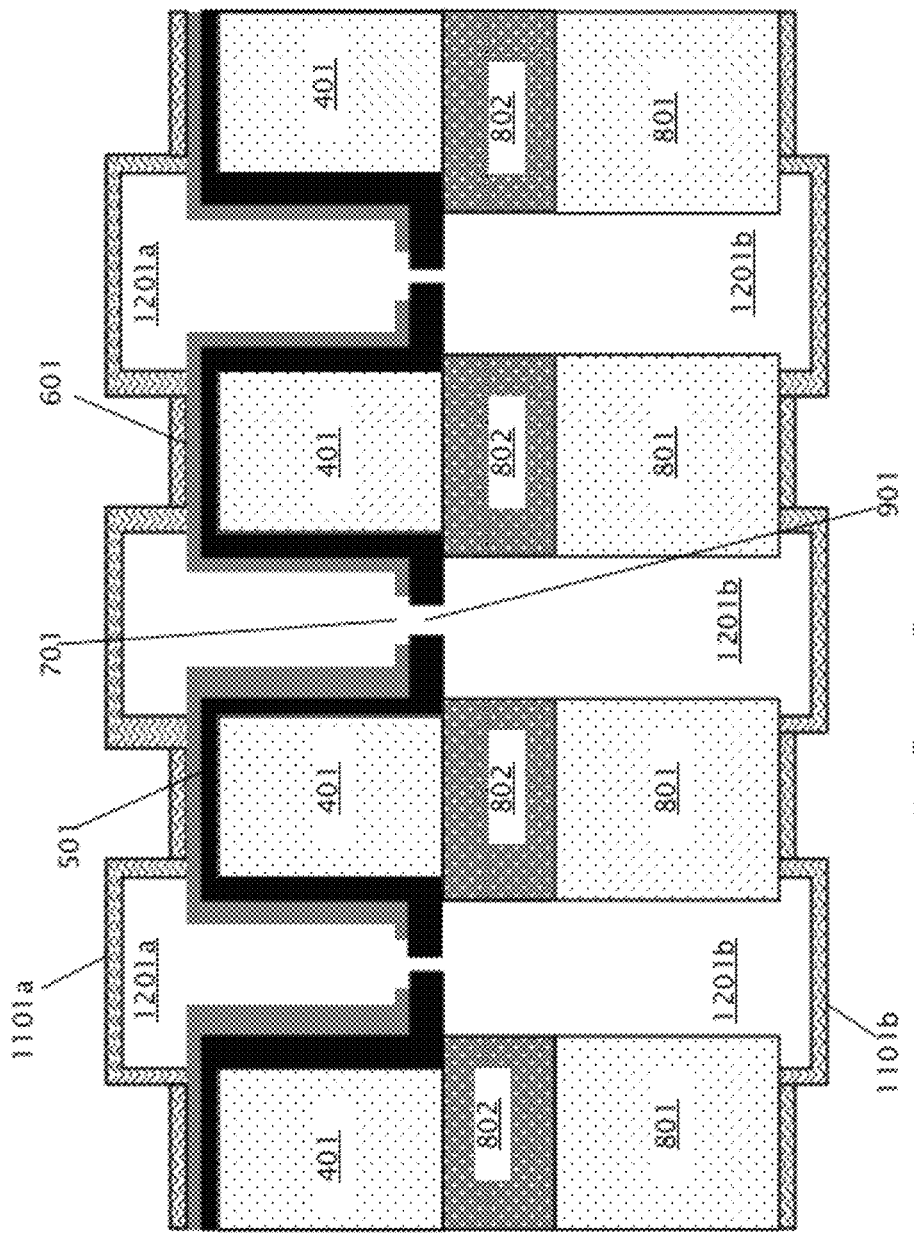
FIG. 12 is a schematic diagram illustrating a cross section of the device of FIG. 11 after removal of the sacrificial material.

After formation of front and back insulating layers 1101a-b, holes corresponding to channel endpoints (shown and discussed below with respect to FIGS. 13 and 14) are formed in the front and back insulating layers 1101a-b. Then, in block 209 of FIG. 2, the sacrificial material 1001 is removed to form front and back channel pairs. FIG. 12 shows the device of FIG. 11 after removal of sacrificial material 1001 to form front channels 1201a and back channels 1201b. Because the sacrificial material 1001 is a thermally decomposable material, the sacrificial material 1001 is removed by heating the device 1100 of FIG. 11 to a temperature at which the sacrificial material 1001 decomposes into gas phases, which escape through the holes corresponding to the channel endpoints in the front and back insulating layers 1101a-b. The sacrificial material removal temperature may be from about 200° C. to about 400° C., depending on decomposition temperature of the sacrificial material 1001, in various embodiments. Front channels 1201a and back channels 1201b comprise self-sealed front and back channel pairs, wherein each pair of front and back channels is connected by a single nanopore 901.

Figure 13:
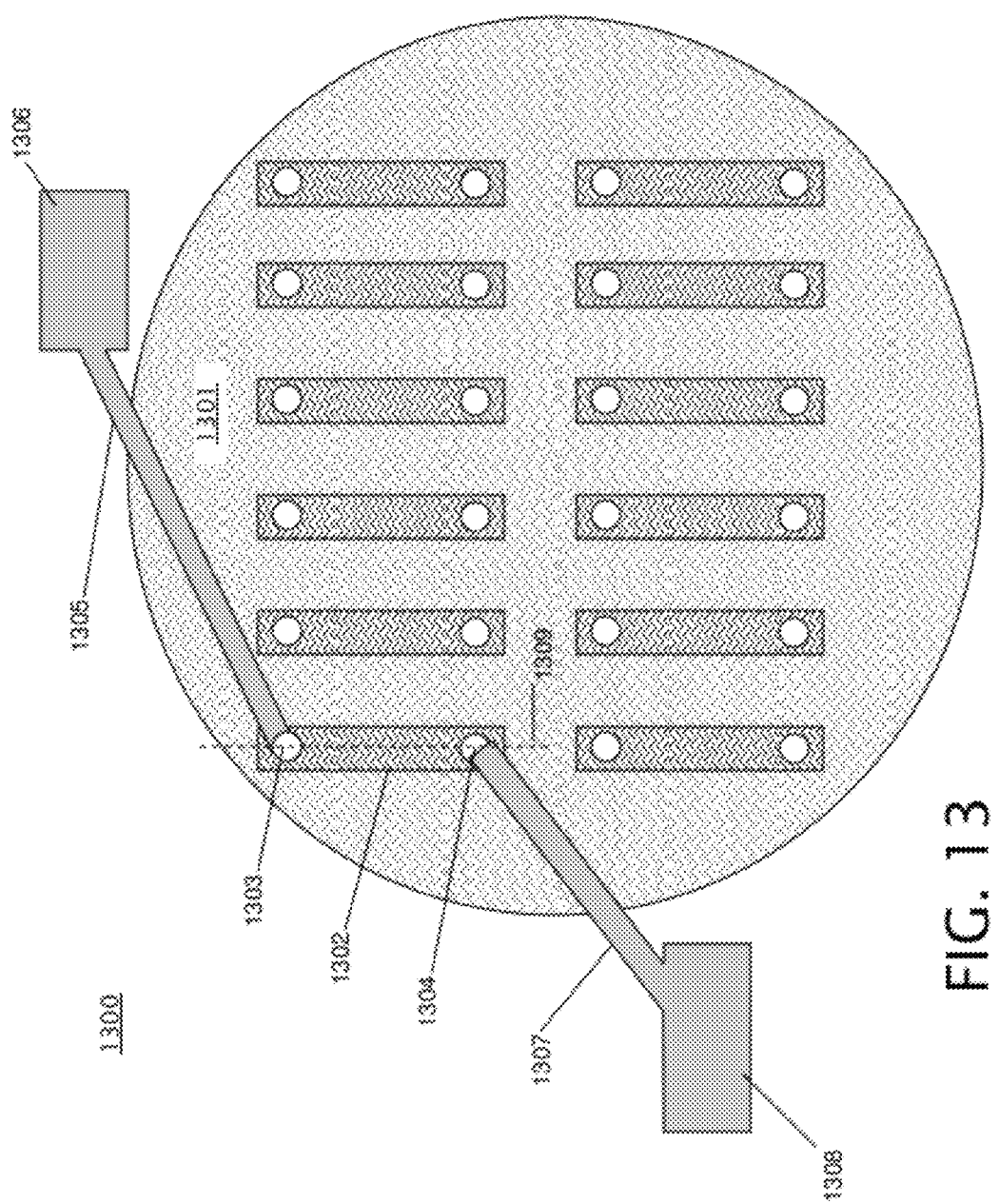
FIG. 13 is a schematic diagram illustrating a top view of a nanopore array including self-sealed fluidic channels formed by the method of FIG. 2.

FIG. 13 is a schematic diagram illustrating a top view of an embodiment of a nanopore array with self-sealed fluidic channels formed by the method of FIG. 2. With reference to FIG. 12, the top view shown in FIG. 13 is looking down at the top insulating layer 1101a of FIG. 12. Device 1300 of FIG. 13 includes a plurality of self-sealed channels, such as channel 1302, arranged on a substrate 1301. Each of the channels shown in FIG. 13 corresponds to a front channel 1201a as shown in FIG. 12, and is connected via a single nanopore (shown in FIG. 14) to a back channel (shown in FIG. 14). Holes 1303 and 1304 are formed on either end of channel 1302, in the top insulating layer 1101a that forms the top surface of the channel 1302. As discussed above with respect to block 209 of FIG. 2, the sacrificial material 1001 escapes through holes 1303 and 1304 after it is thermally decomposed. The holes 1303 and 1304 are connected to external fluidic reservoirs 1306 and 1308 via tubes 1305 and 1307. The fluidic reservoirs 1306 and 1308 hold a liquid, such as an ionic buffer, that contains DNA to be analyzed by the nanopore associated with channel 1302. Fluidic reservoirs 1306 and 1308 may comprise syringes in some embodiments. One of tubes 1305 and 1307 may be a fluidic outlet from channel 1302, and the other may be a fluidic inlet to load the liquid into channel 1302, causing the liquid to flow from one end of the channel 1302 to the other. The other channels shown on the front side of substrate 1301 in FIG. 13 may also be connected to respective fluidic reservoirs and tubes, similarly to channel 1302, as well as the back channels located on the other side of the substrate 1301. Each channel shown on substrate 1301 is connected to a single nanopore, and each nanopore is individually addressable and may be used individually for DNA sequencing, allowing sequencing to be performed in parallel by the nanopores in nanopore array 1300. FIG. 13 is shown for illustrative purposes only; a nanopore array with self-sealed fluidic channels may include any appropriate number of nanopores with associated front and back channel pairs.

Figure 14:
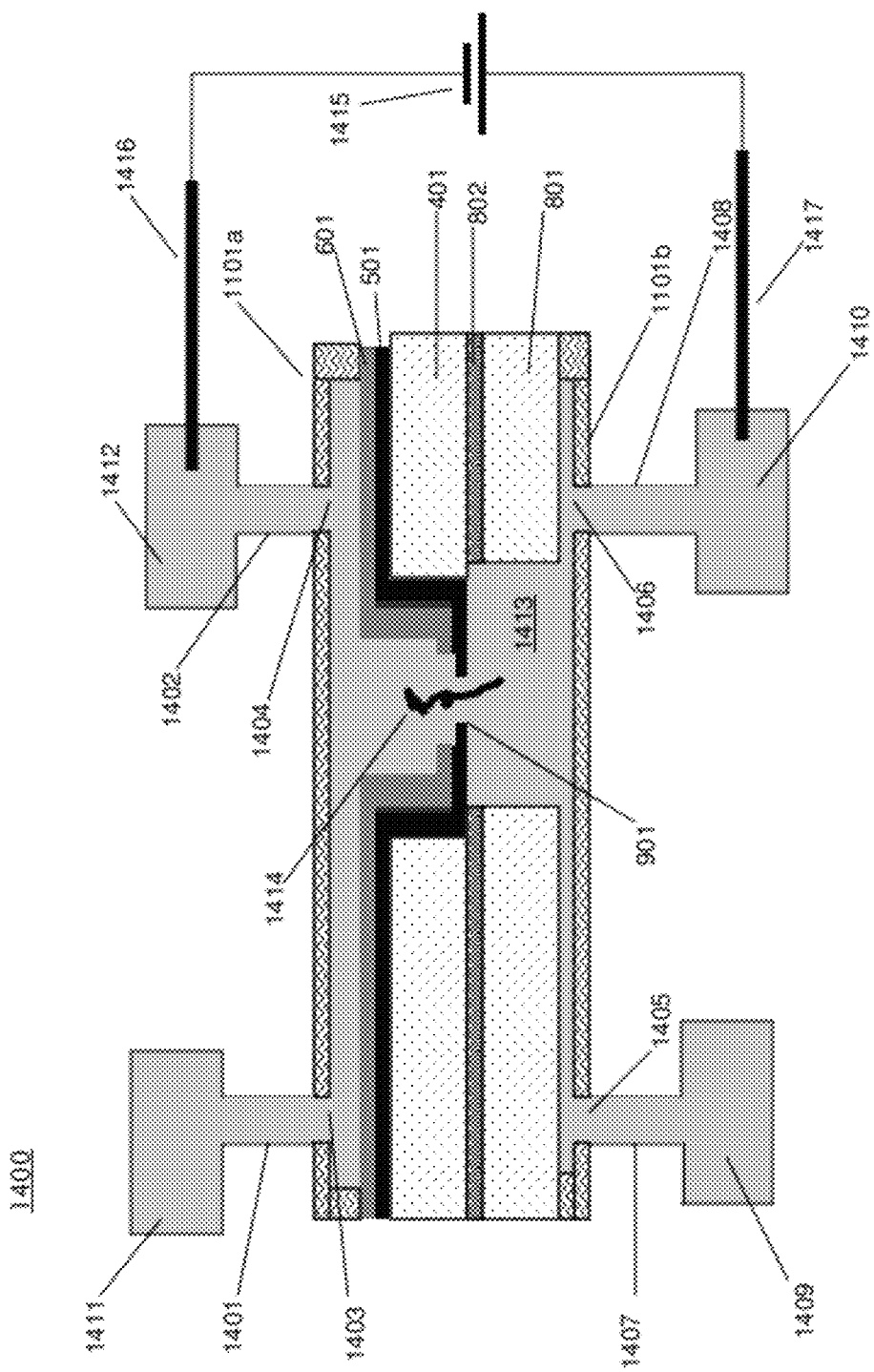
FIG. 14 is a schematic diagram illustrating a cross section of one nanopore of the nanopore array of FIG. 13.

FIG. 14 shows a cross-section of channel 1302 of FIG. 13 along dashed line 1309 during a DNA translocation experiment. Holes 1403 and 1404 are openings to the front channel, corresponding to holes 1303 and 1304 of FIG. 13, tubes 1401 and 1402 correspond to tubes 1305 and 1307 of FIG. 13, and fluidic reservoirs 1411 and 1412 correspond to fluidic reservoirs 1306 and 1308 of FIG. 13. Holes 1405 and 1406 are openings into the back channel. Tube 1407 connects fluidic reservoir 1409 to hole 1405, and tube 1408 connects fluidic reservoir 1410 to hole 1406. Fluid 1413, containing DNA molecules such as DNA molecule 1414, from fluidic sources 1409, 1410, 1411 and/or 1412 fills the front and back channels, and also fills the nanopore 901. Because DNA is negatively charged, the battery configuration of electrical voltage bias 415 will cause the DNA to move from the top chamber to bottom chamber. So, in embodiments that include a battery configuration such as electrical voltage bias 1415, DNA 1414 will be initially loaded on to top chamber only. During the measurement, DNA 1414 will move from the top chamber to the bottom chamber through the nanopore 901. The DNA molecule 1414 is translocated through nanopore 901 by the electrical voltage bias 1415 that is applied across the nanopore 901 via two electrochemical electrodes 1416 and 1417, which are dipped in the fluid in fluidic reservoirs 1412 and 1410 respectively. As the DNA molecule 1414 is translocated through nanopore 901, the DNA molecule 1414 passes through the nanopore 901 base by base, allowing sequencing of the DNA 1414. FIG. 14 shows patterned back layer 801, patterned buried layer 802, patterned front layer 401, membrane 501, mechanical support layer 601, and front and back insulating layers 1101a-b. The front channel is bounded by front insulating layer 1101a, and the back channel is bounded by back insulating layer 1101b.

Figure 15A:
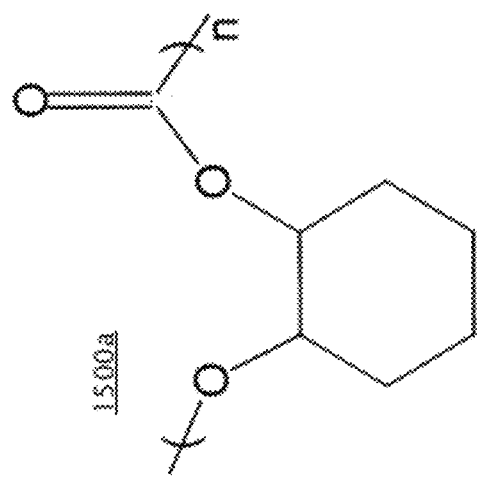
FIGS. 15a-b illustrates thermally decomposable polymers that may be used for the sacrificial material in various embodiments.
Figure 15B:
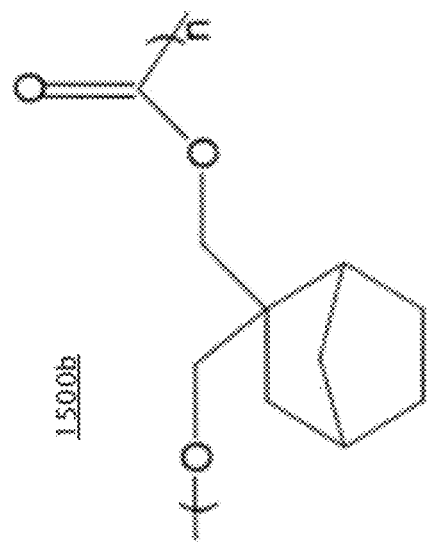

FIGS. 15a-b show examples of thermally decomposable polymers that may be used for sacrificial material 1001. FIG. 15a shows polypropylene carbonate (PPC) 1500a, and FIG. 15b shows polynorborene carbonate (PNC) 1500b. Some PPC-based materials, such as shown in FIG. 15a, may be decomposed at a temperature from about 200 to about 350° C. Some PNC-based materials, such as shown in FIG. 15b, may be decomposed at a temperature from about 250 to about 400° C. Both PPC and PNC based materials are primarily converted into gaseous $H_2O$ and $CO_2$ by thermal decomposition.

The technical effects and benefits of exemplary embodiments include formation of channels for a nanopore array that may be used for parallel DNA sequencing without wafer bonding.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A nanopore array, comprising:
    a plurality of front and back channel pairs located in a substrate, wherein the front channel of each channel pair is connected to the back channel of its respective channel pair by a single nanopore of a plurality of nanopores, wherein the nanopores are formed through a membrane layer that is located between the front channels and the back channels;
    wherein the plurality of front channels of the plurality of front and back channel pairs are located in a patterned front layer of the substrate and bounded on top by a front insulating layer;
    wherein the membrane layer is located over the patterned front layer of the substrate and in a bottom portion of the plurality of front channels;
    wherein the plurality of back channels of the plurality of front and back channel pairs are located in a patterned buried layer and a patterned back layer of the substrate and bounded at the bottom by a back insulating layer, and
    a top of the front insulating layer above each front channel comprises a plurality of holes and a bottom of the back insulating layer comprises a plurality of holes under each of the back channels, wherein each of the plurality of holes is connected to a corresponding fluidic source.

2. The nanopore array of claim 1, wherein the patterned front and back layers of the substrate comprise silicon, the patterned buried layer of the substrate comprises an oxide, the membrane layer comprises one of silicon nitride and graphene, and the front and back insulating layers comprise silicon nitride.

3. The nanopore array of claim 1, further comprising a mechanical support layer, the mechanical support layer being located over the membrane layer and in the front channels, the mechanical support layer comprising windows in which the nanopores are located.

4. The nanopore array of claim 3, wherein the mechanical support layer comprises a first layer of silicon oxide formed adjacent to the membrane layer, and a second layer of silicon nitride formed over the first layer of silicon oxide.

5. The nanopore array of claim 4, wherein the first layer of silicon oxide has a thickness of about 200 nm, and the second layer of silicon nitride has a thickness of about 200 nm.

6. The nanopore array of claim 1, wherein the membrane layer is about 20 nm thick.

* * * * *